United States Patent [19]

Hoffman

[11] 4,279,255

[45] Jul. 21, 1981

[54] LOCALIZED BODY HEAT APPLICATOR DEVICE

[75] Inventor: John C. Hoffman, Severna Park, Md.

[73] Assignee: John F. Taylor, Severna Park, Md.; a part interest

[21] Appl. No.: 124,940

[22] Filed: Feb. 26, 1980

[51] Int. Cl.³ .......................... A61F 7/00; H05B 3/06
[52] U.S. Cl. ................................. 128/402; 128/399; 219/211; 219/527; 219/528; 219/535; 219/549
[58] Field of Search .............. 219/211, 212, 313, 523, 219/527, 528, 535, 549; 338/212; 128/384, 387, 399, 400, 401, 402, 403, 404; 320/40

[56] References Cited

U.S. PATENT DOCUMENTS

| | | | |
|---|---|---|---|
| 2,842,655 | 7/1958 | Schwebel | 219/527 |
| 3,079,486 | 2/1963 | Winchell | 219/211 |
| 3,084,241 | 4/1963 | Carrona | 219/211 |
| 3,407,818 | 10/1968 | Contanzo | 128/384 |
| 3,445,748 | 5/1969 | Delatorre | 320/40 |
| 3,465,120 | 9/1969 | Merna | 219/211 |
| 3,644,706 | 2/1972 | Larenzo | 219/211 |
| 3,857,397 | 12/1974 | Brosseau | 128/384 |
| 4,201,218 | 5/1980 | Feldman | 128/402 |

Primary Examiner—Volodymyr Y. Mayewsky
Attorney, Agent, or Firm—Cushman, Darby & Cushman

[57] ABSTRACT

A portable therapeutic heating device is provided that may be readily worn and transported by a user. A flexible heating unit is attached to a body part and is capable of raising the skin temperature of that body part to about 102°–108° F. The flexible heating unit includes a plurality of distinct sets of electric resistance heating elements. The flexible heating unit is connected by a flexible tape to a battery pack which is mounted to the approximate center of gravity of the user's body. A switch is mounted on the battery pack, and provides for selection of which sets of electric resistance heating elements will be energized by a battery received by the battery pack, to thereby vary the amount of heat applied by the heating unit to a body part. The switch is mounted in a cutout formed in a casing defining the battery pack. A pair of rechargeable lead-acid "D" batteries are desirably received by the battery pack, and circuitry is provided for indicating when the voltage of a rechargeable battery received by the battery pack reaches a predetermined value below the rated value of the battery. A printed circuit board is mounted completely covering the batteries in the battery pack casing, between the batteries and the casing top, with all of the necessary electrical components operatively connected to the printed circuit board.

12 Claims, 5 Drawing Figures

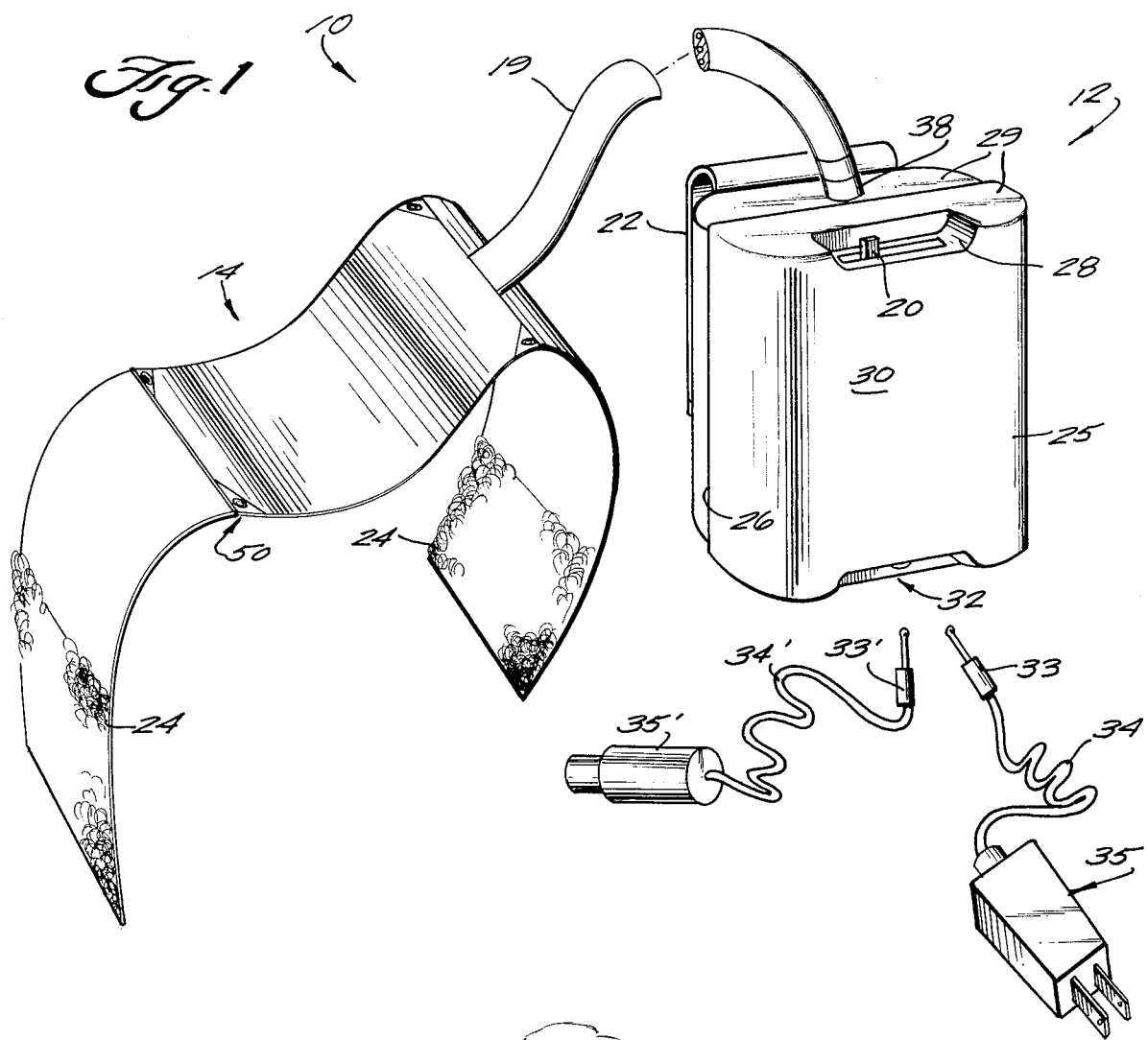
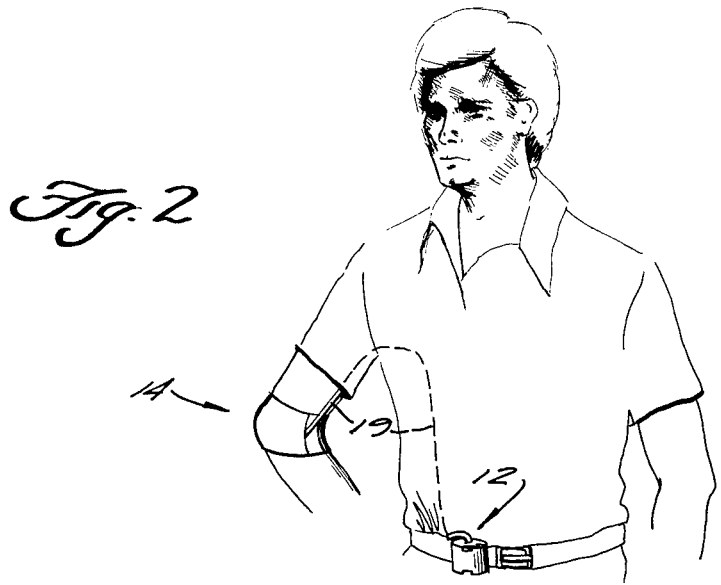

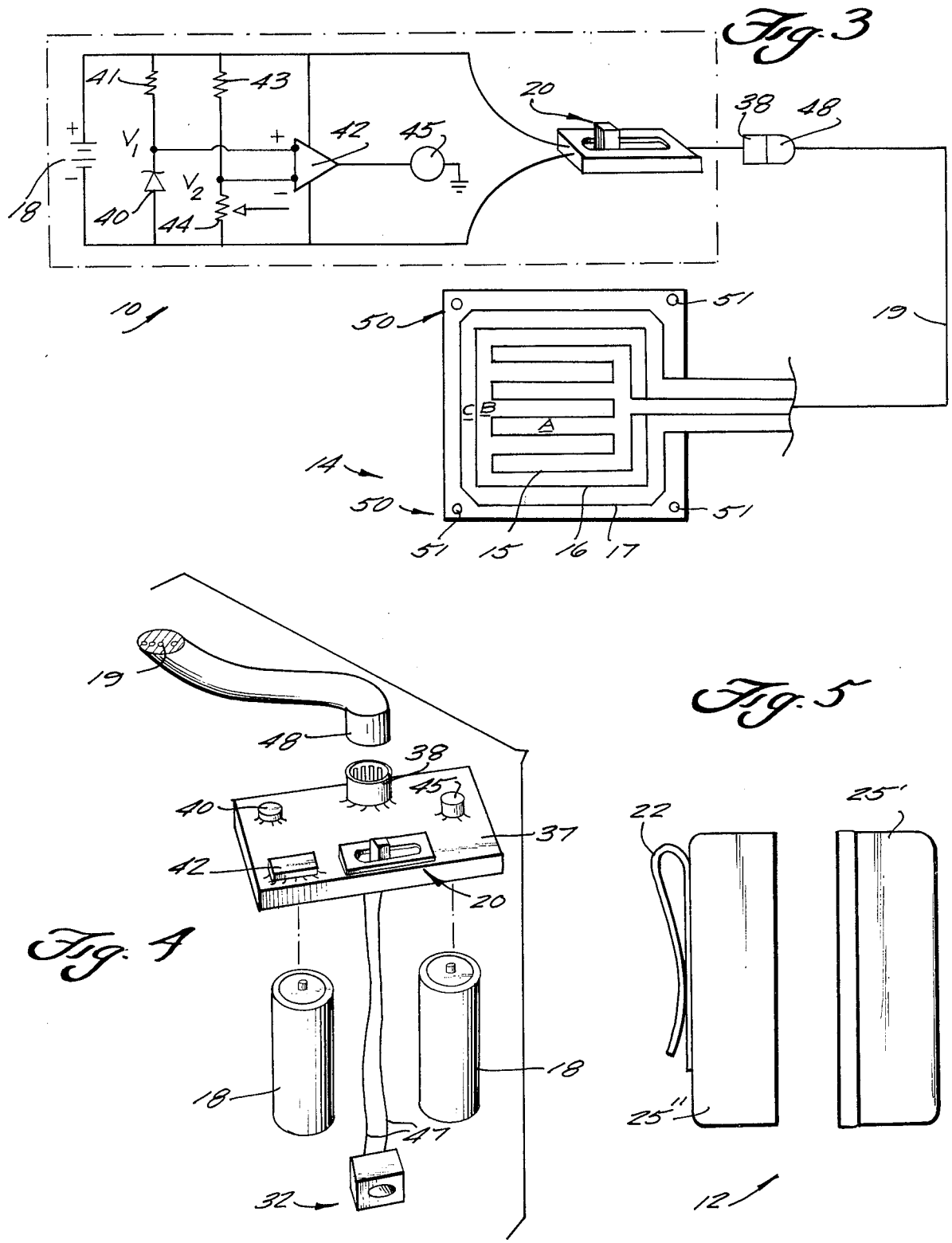

LOCALIZED BODY HEAT APPLICATOR DEVICE

BACKGROUND AND SUMMARY OF THE INVENTION

The invention relates to a portable therapeutic device, one especially adapted to be worn by a user while therapeutic heat is being applied to a portion of the user's body.

There have been provisions for application of heat to an individual's body utilizing heat sources worn by the user, in the past. Such devices have usually been for the purposes of keeping the user warm, such as shown in U.S. Pat. Nos. 3,079,486 and 3,084,241. However there have been suggestions in the past (see co-pending application Ser. No. 972,346 filed Dec. 22, 1978, now U.S. Pat. No. 4,201,218) for applying heat to body portions for therapeutic purposes. Heretofore, however, proposed devices have had a number of problems associated therewith that limited their applicability for applying therapeutic heat to body portions. In particular, prior proposed devices have been incapable of providing sufficient amounts of heat over sufficient periods of time to be really useful for therapeutic purposes. Also, proposed devices have incorporated the power sources directly with the heat applying structures, making the mounting thereof on body portions cumbersome, and interfering with normal physical activities. Other problems inherent in prior proposed devices include costs of manufacture, difficulties of manufacture, or lack of adaptability.

According to the present invention a portable therapeutic heating device is provided which overcomes most of the drawbacks inherent in the prior art proposals. A device according to the present invention is capable of heating a body portion so that the skin temperature reaches 102°–108° F., and is capable of supplying heat for periods of about four to five hours, long enough to have significant therapeutic benefits. The device according to the invention is utilized so that it does not interfere with normal activity, and can be worn by the user while performing most normal functions. The inventive device can be constructed from off-the-shelf components, and utilizes batteries that are readily rechargeable. In order to protect the batteries, an indicator is provided for indicating when the voltage of a battery utilized reaches a predetermined value below the rated value of the battery. The inventive device is also simple and easy to construct and utilize, with minimum chances of damage and with maximum adaptability.

A portable therapeutic device according to the invention comprises two main components, a battery pack adapted to receive at least one battery therein, and means for applying heat to a localized portion of the body so that the skin temperature of that body portion reaches about 102°–108° F., said means comprising a flexible heating unit having a plurality of distinct sets of electrical resistance heating elements associated therewith. Electrical interconnection means are provided for operatively interconnecting the battery received by the battery pack to the heat applying means electric resistance heating element sets. The electrical interconnection means preferably comprises a flexible flat tape providing the only connection between the battery pack and the heating unit, such means being dimensioned so that the heat applying means may be positioned on body parts remote from the center of gravity of the body while the battery pack is mounted at the body center of gravity. Means are provided for providing ready attachment of the battery pack to the approximate center of gravity of one's body, and means are provided for providing ready attachment of the heat applying means to a body part in therapeutic heat applicating association therewith. Selector switch means are operatively associated with the electrical connection means and attached to the battery pack for selecting which of the sets of electric resistance heating elements will be energized by a battery received by the battery pack to thereby vary the amount of heat applied by the heating means to a body part.

The battery pack preferably is adapted to receive at least one rechargeable battery, preferably two "D" 2-volt, in series, lead-acid rechargeable batteries, having a combined voltage of four volts. The device further comprises charging circuitry means and a charger plug receptacle mounted on the battery pack for receipt of a charger plug for effecting recharging of a rechargeable battery received by the battery pack, and circuitry means are provided operatively associated with the electrical interconnection means and attached to the battery pack for indicating when the voltage of the rechargeable battery or batteries received by the battery pack reaches a predetermined value below the rated value of the battery or batteries.

The battery pack includes a casing having a top surface and side surfaces, and a cutout is defined in the casing at the interface of the top surface and a side surface with the selector switch mounted in the cutout. Another cutout can be provided for a plug for providing plugging of the electrical interconnection means into the battery pack, and another cutout for the recharger plug. A printed circuit board is provided under the casing cover and completely covering the battery or batteries, all of the electrical components being mounted on the printed circuit board.

The heat applying means may comprise a wide variety of conventional heat applicator structures which are particularly constructed for therapeutic heat application. For instance, the heat applying means may comprise a silicone rubber flexible heating unit with the electric resistance heating elements comprising multi-stranded nickel alloy resistance wire elements. Three distinct sets of electric resistance heating elements may be provided, each set when switched in causing the raising of a larger area to a lower temperature than without such sets switched in. Alternatively the heat applying means may comprise an etched foil heating unit, or the like.

It is the primary object of the present invention to provide an effective portable therapeutic device. This and other objects of the invention will become clear from an inspection of the detailed description of the invention, and from the appended claims.

BRIEF DESCRIPTION OF THE DRAWINGS

FIG. 1 is a perspective view showing an exemplary device according to the present invention;

FIG. 2 is a perspective view showing the device of FIG. 1 in use for applying heat to a user's elbow;

FIG. 3 is a schematic circuit diagram illustrating many of the main electrical components of the device of FIG. 1;

FIG. 4 is an exploded perspective view illustrating some of the interior battery pack components; and FIG. 5 is a side view showing the casing of the battery pack illustrated in FIG. 1 with the casing halves spaced apart.

DETAILED DESCRIPTION OF THE DRAWINGS

A portable therapeutic heating device according to the present invention is shown generally at 10 in the drawings. The two main components of the device 10 include a battery pack 12 adapted to receive at least one battery therein, and means for applying heat to a localized portion of the body so that the skin temperature of that body portion reaches about 102°–108° F., said means comprising a flexible heating unit 14 having a plurality of distinct sets (e.g. 15, 16, 17—see FIG. 3) of electric resistance heating elements associated therewith.

The device 10 further comprises electrical interconnection means for operatively electrically interconnecting a battery (or batteries) 18 received by the battery pack 12 to the heat applying means 14 electric resistance heating elements sets 15–17, the electrical interconnection means being dimensioned so that the heat applying means 14 may be positioned on body parts remote from the center of gravity of the body while the battery pack is mounted approximately at the body center of gravity (see FIG. 2). Preferably the electrical interconnection means comprises a flat tape 19 (see FIGS. 1 and 4 in particular) which may comprise a four conductor wire 24 gauge 1936 bundle with PVC that is very flexible comprising the insulation. A cross-section of the electrical interconnection means 19 is illustrated in FIG. 4. The device 10 further comprises a selector switch 20 operatively associated with the electrical connection means 19 and attached to the battery pack 12 for selecting which of the sets 15–17 of heating elements will be energized by a battery (18) received by the battery pack to thereby vary the amount of heat applied by the heating means to a body part. The device 10 further comprises means for providing ready attachment of the battery pack to the approximate center of gravity of one's body, such as belt clip 22, and means for providing ready attachment of the flexible heating unit to a body part in therapeutic heat application association therewith so that the temperature of the body part can be elevated to 102°–108° F. by the heating means, such as the VELCRO strips 24 attached to the sides of the flexible heating unit 14.

The battery pack 12 includes a casing 25, which preferably is formed in two halves 25', 25", as illustrated in FIG. 5. The casing halves 25', 25" are preferably made of plastic, such as molded from ABS with a junction line 26 therebetween. The half 25" has a belt clip 22 associated therewith, and the casing halves are provided so that the junction line 26 is vertical when the casing 25 is mounted by the belt clip 22 at a user's approximate center of gravity. The casing 25 includes at least one cutout 28 (see FIG. 1) formed therein, the cutout being provided in the casing 25 at the interface of the top surface 29 with a side surface 30. The selector switch 20 is mounted in the cutout 28 so that no portion thereof extends beyond a surface providing a continuation of the top 29 and side 30 surfaces of the casing 25 at the cutout 28. Thus, when the casing is viewed from the side, as indicated in FIG. 5, the selector switch 20 cannot be seen. In mounting the selector switch in this way maximum protection is provided therefor and there is minimum possibility that it can catch on extraneous articles, or the like, and damage them or allow them to effect damage to it.

The casing 25 also includes a charger plug receptacle 32 mounted on the bottom thereof for receipt of a plug 33, 33' from a recharger unit. The recharger plug receptacle 32, and associated circuitry are preferably designed so that recharging of the batteries 18 received by the battery pack 12 can be accomplished by both a 120-volt A.C. source, or a 12-volt D.C. source (e.g. automobile). For instance, the plug 33 is connected to a cord 34 which in turn is connected to a plug assembly 35 for a 120-volt A.C. outlet, while the plug 33' is connected by cord 33' to a plug structure 35' for insertion into an automobile cigarette plug or the like.

Preferably the batteries 18 (see FIG. 2) received by the battery pack 12 are rechargeable "D" lead-acid rechargeable batteries. Preferably two such batteries are provided, connected in series, providing a total of four volts. The batteries 18 are received within the casing 25 with a printed circuit board 37 (see FIG. 4) completely covering the tops thereof and disposed between the batteries 18 and the top 29 of the casing 25. The casing is constructed so that an opening is provided therein through which the actuator for the selector switch 20 extends (see FIG. 1), and so that an opening is provided for a male plug 38 for the electrical interconnection means 19 in the casing top 29.

The device 10 also comprises circuitry means operatively associated with the electrical interconnection means 19 and operatively attached to the battery pack 12 for indicating when the voltage of a rechargeable battery or batteries 18 received the battery pack 12 reaches a predetermined value below the rated value of the rechargeable batteries. Such circuitry means, as shown most clearly in FIGS. 3 and 4, preferably include a Zener diode 40 and resistor 41 operatively connected between batteries 18 and one terminal of a solid-state voltage comparator 42, a resistor 43 and the variable resistor 44 operatively connected between the batteries 18 and the other input terminal of the voltage comparator 42, and a buzzer 45, such as the type described in U.S. Pat. No. 3,974,499, connected to the output from the voltage comparator 42. All of the components 40–45, as well as the leads therebetween, are affixed to or are a part of the printed circuit board 37. The recharger plug jack 32 is also operatively connected to the printed circuit board 37, wires 47 or the like leading from the receptacle 32 between the batteries 18 to the printed circuit board 37.

The electrical interconnection means 19 is connected through a leak-proof connection at one end thereof to the flexible heating unit 14, and at the other end thereof a female plug 48 is provided, which plug is compatible with the male plug 38 mounted on the printed circuit board 37.

The flexible heating unit 14 may take a wide variety of forms. One particular form it may take that is particularly desirable is that of a silicone rubber flexible heating unit, such as the general type sold by Electro-Flex Heat, Inc. of Bloomfield, Conn., under the name "Silicone Rubber/Fiberglass Stock Heaters." Multi-stranded nickel alloy resistance wire elements are provided as the electric resistance heating elements. Another form the flexible heating unit 14 may take is that of an etched foil heating unit, such as available from Safeway Products, Inc. of Middletown, Conn.

Whatever form the flexible heating unit 14 takes, a plurality of electric resistance heating elements are provided in sets associated therewith, such as sets 15, 16 and 17. For instance the set 15 may comprise the primary heating set, and is disposed centrally of the heating unit 14, with the set 16 disposed around the set 15 and the set 17 around the set 16. The outermost set 17 is designed so that no portions thereof extend into the corners 50 of the flexible heating unit 14 so that grommets 51 or the like may be mounted in such corners for ultimate attachment to the means 24 for fastening the heating unit 14 to a body part. As previously stated, the means 24 may comprise VELCRO straps, or straps with snap fasteners, or any other suitable conventional fastening means.

The electric resistance heating elements sets 15-17 are operatively connected to the selector switch 20, which also is connected to the batteries 18 (see FIG. 3) so that by moving the actuator for the selector switch 20 between its four positions either no current will be supplied to the electric resistance units 15-17, current will be supplied only to the first set 15, current will be supplied to both the first and second sets 15, 16, or current will be supplied to all three sets 15-17. Once switch 20 is in a position supplying current to only the first set 15, a given area A (e.g. 7.0 square inches) of the unit 14 raises the skin temperature of the body part to which it is applied to about 108° F. When the switch 20 is in the position of selecting both the sets 15 and 16, current is supplied to a given area B (e.g. 7.79 square inches) of the unit 14 and the body part thereunder so that the skin temperature of the body part is raised to about 150° F. When the third set 17 is selected along with the first and second sets 15, 16, current is supplied to a third area C (e.g. 8.75 square inches) of the unit 14 to raise the temperature of the underlying body part to about 102° F. Utilizing two 2.0 volt lead-acid rechargeable batteries according to the present invention as the power source, it is possible to maintain the 108° F. temperature for about four hours, the 105° F. temperature for about four and one half hours, and the 102° F. temperature for about five hours.

An exemplary structure according to the present invention having been described, an exemplary manner of use thereof will now be set forth:

The plugs 38, 48 are disconnected, and the straps 24 wrapped around a body part (such as the elbow—see FIG. 2) to bring the flexible heating unit 14 into intimate contact with the portion of the body part to which therapeutic heat is desirably applied. Then the electrical interconnection 19 (which preferably is about 40 inches long) is run under the clothing from the flexible heating unit 14 to a position adjacent the user's center of gravity, where the battery pack 12 is to be mounted. The battery pack 12 is mounted to the user by putting the clip 22 over the user's belt (see FIG. 2), and then the female plug 48 from the electrical interconnection 19 is plugged into the male plug 38 associated with the printed circuit board 37 received within the casing 25 to place the device 10 in position for use.

When it is desired to apply therapeutic heat, the user merely moves the actuator of the selector switch 20 to the appropriate position, energizing one, two, or all of the electric resistance heating sets 15-17 to apply therapeutic heat to the particular body part (e.g. elbow). Once the selector switch 20 is set in the appropriate position, the user may go about his normal activities, the device 10 not interfering therewith but therapeutic heat being applied all the times. When it is desired to terminate application of therapeutic heat, the actuator for the selector switch 20 is merely moved to the inoperative position, cutting off the flow of current from the batteries 18 within the battery pack 12 to the flexible heating unit 14.

If during use the voltage of the batteries 18 drops below a predetermined value (e.g. 3.6 volts), an indicator will be activated. The components 40-45 are operatively connected to the batteries 18, and the variable resistance of the resistor 44 is set, so that the voltages $V_1$, $V_2$ (see FIG. 3) are equal when the battery 18 is at 4.0 volts. If $V_1$ becomes greater than $V_2$, comparator 42 energizes the buzzer 45. The Zener diode 40, and the values of the resistances 41, 43, 44, are selected so that when the voltage of the batteries 18 drops to 3.6 volts, voltage $V_1$ is greater than voltage $V_2$, which energizes buzzer 45.

Once the buzzer 45 is energized, it is possible to turn it off only by turning the selector switch 20 to the off position. Then the batteries may be recharged, either from a 120 A.C. source, or from a 12-volt D.C. source, by inserting jack 33 or jack 33', respectively into recharger receptacle 32, and connecting it to the respective power source utilizing plug 35 or plug 35', respectively. Overcharging protection is inherently provided with conventional circuitry associated with the receptacle 32 (which may be mounted on printed circuit board 37), and once recharging is completed the device 10 is ready for reuse.

The battery pack 12 is assembled by placing the printed circuit board underneath the top surface 29 of the casing halves 25', 25'', so that the actuator for selector switch 20 and the male plug 38 extend outwardly through the top surface 29; placing the two batteries 18 in the casing; and closing the casing halves 25', 25'' together and sealing them shut.

It will thus be seen that according to the present invention a simple and effective portable therapeutic heat applicator device has been provided that provides adequate application of therapeutic heat while not interfering with normal body functions. While the invention has been herein shown and described in what is presently conceived to be the most practical and preferred embodiment thereof, it will be apparent to those of ordinary skill in the art that many modifications may be made thereof within the scope of the invention, which scope is to be accorded to broadest interpretation of the appended claims so as to encompass all equivalent structures and devices.

What is claimed is:

1. A portable therapeutic heating device, comprising
means for applying heat to a localized portion of the body so that the skin temperature of that body reaches about 102°–108° F., said means comprising a flexible heating unit having a plurality of distinct sets of electric resistance heating elements associated therewith;
a battery pack adapted to receive at least one battery;
electrical interconnection means for operatively electrically interconnecting a battery received in said battery pack to said heat applying means electric resistance heating elements sets, said electrical interconnection means being dimensioned so that said heat applying means may be positioned on body parts remote from the center of gravity of the body while the battery pack is mounted approximately at the body center of gravity;
selector switch means operatively associated with said electrical connection means and attached to said battery pack for selecting which of said sets of electric resistance heating elements will be energized by a battery received by said battery pack to thereby vary the amount of heat applied by said heating means to a body part;

means for providing for ready attachment of said battery pack to the approximate center of gravity of one's body; and means for providing for ready attachment of said heat applying means to a body part in therapeutic heat application association therewith so that the skin temperature of the body part can be elevated to about 102°–108° F. by said heating means.

2. A device as recited in claim 1 wherein said battery pack is adapted to receive a rechargeable battery, and further comprising charging circuitry means and a charger plug receptacle mounted with said battery pack for receipt of a charger plug for effecting recharging of a rechargeable battery received by said battery pack, and circuitry means operatively attached to said battery pack for indicating when the voltage of a rechargeable battery received by said battery pack reaches a predetermined value below the rated value of such a rechargeable battery.

3. A device as recited in claim 2 wherein said heat applying means comprises a silicone rubber flexible heating unit, and wherein said electric resistance heating elements comprise multi-stranded nickel alloy resistance wire elements.

4. A device as recited in claim 2 wherein said heat applying means comprises an etched foil heating unit.

5. A device as recited in claim 2 wherein three distinct sets of electric resistance heating elements are provided, a first set when selected by said selector switch means being capable of raising skin temperature of a given area of a body part A to which it is applied to about 108° F.; a second set when selected by said selector switch means with said first set being capable of raising skin temperature of a given area of a body part B to about 105° F., wherein B>A; and a third set which when selected with said first and second sets is capable of raising skin temperature of a given area C of a body part to about 102° F., wherein C>B.

6. A device as recited in claim 2 wherein said battery pack comprises a casing having a top surface and side surfaces, and including means defining a cutout in said casing at the interface of said top surface and a side surface, said selector switch mounted in said cutout so that no portion thereof extends beyond a surface providing a continuation of said top and side surfaces at said cutout.

7. A device as recited in claim 6 wherein said means for providing ready attachment of said battery pack to the approximate center of gravity of one's body comprising means for attaching said battery pack to a belt.

8. A device as recited in claim 2 wherein said electrical interconnection means consists essentially of a flexible tape of electrical insulation material having electrical wires disposed therein extending between said heat applying means and said battery pack, no physical interconnection being provided between said heat applying means and said battery pack besides said tape.

9. A device as recited in claim 2 wherein said battery pack comprises a casing with at least one rechargeable battery disposed therein; a printed circuit board completely covering said at least one battery disposed between the top of the casing and said at least one battery; said battery voltage indicating circuitry means comprising a plurality of components each operatively attached to or formed with said printed circuit board; said selector switch means operatively connected to said printed circuit board and extending upwardly from the top thereof and through an opening in said casing for receipt thereof; a first electrical plug component operatively connected to said printed circuit board and extending upwardly from the top thereof, and through an opening in said casing for receipt thereof; and said electrical interconnection means including a second electrical plug component formed on an end thereof remote from said heating means, said second plug component for cooperation with said first plug component to operatively attach said heating means to said battery.

10. A device as recited in claim 9 wherein said at least one rechargeable battery comprises a pair of series connected lead-acid "D" rechargeable batteries having a combined voltage of about 4.0 volts; and wherein said battery voltage indicating circuitry means includes a buzzer for indicating when said battery voltage drops below about 3.6 volts.

11. A device as recited in claim 9 wherein said casing is formed of two plastic halves with a junction line therebetween, one half having a belt clip associated therewith, and said junction line being vertical when said casing is mounted by said belt clip at a user's approximate center of gravity.

12. A device as recited in claim 2 wherein said battery voltage indicating circuitry means comprises a Zener diode, voltage comparator, and buzzer operatively connected together so that said buzzer is activated when the battery voltage drops below a preselected minimum.

* * * * *